US006530371B2

(12) United States Patent
Jansen et al.

(10) Patent No.: US 6,530,371 B2
(45) Date of Patent: *Mar. 11, 2003

(54) DRUG DELIVERY SYSTEM INCLUDING HOLDER AND DRUG CONTAINER

(75) Inventors: Hubert Jansen, Poisat (FR); Lionel Vedrine, Saint Martin d'Heres (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/993,098

(22) Filed: Nov. 5, 2001

(65) Prior Publication Data

US 2002/0035349 A1 Mar. 21, 2002

Related U.S. Application Data

(63) Continuation of application No. 09/417,346, filed on Oct. 14, 1999, now Pat. No. 6,382,204.

(51) Int. Cl.[7] ............................................. A61M 11/00
(52) U.S. Cl. .................. 128/200.19; 604/218
(58) Field of Search ................. 128/200.14, 200.18, 128/200.19, 200.22, 203.21, 203.22, 203.28, 205.13–205.16; 604/218, 131, 134, 135, 208, 187, 188, 232

(56) References Cited

U.S. PATENT DOCUMENTS

| D212,991 S | 12/1968 | Evers et al. |
| D226,767 S | 4/1973 | Dragen |
| 3,874,380 A | 4/1975 | Baum |
| 3,874,381 A | 4/1975 | Baum |
| 4,060,073 A | 11/1977 | Collica et al. ............... 128/1.1 |
| 4,061,254 A | 12/1977 | Nilson |
| 4,235,235 A | 11/1980 | Bekkering |
| 4,344,573 A | 8/1982 | De Felice |
| 4,405,308 A | 9/1983 | Jessup |
| 4,583,978 A | 4/1986 | Porat et al. ................. 604/208 |

(List continued on next page.)

FOREIGN PATENT DOCUMENTS

| DE | 199 44 209 A1 | 9/1999 |
| EP | 0452728 A1 | 10/1991 |
| EP | 0334349 B1 | 2/1992 |
| EP | 0546607 B1 | 11/1992 |

(List continued on next page.)

*Primary Examiner*—Aaron J. Lewis
*Assistant Examiner*—Teena Mitchell
(74) *Attorney, Agent, or Firm*—Allen W. Wark

(57) ABSTRACT

A drug delivery system for administering preset doses of a substance such as a drug, vaccine or the like is provided. The drug delivery system includes a holder and a pre-filled drug container such as a syringe which is securely retained in the holder. The drug container includes a barrel for containing the substance, a movable stopper situated within the barrel, and a blunt end having an opening through which the substance within the barrel can be expelled. The holder includes a distal portion and a proximal portion, each configured to accommodate the drug container, with the distal portion being able to be assembled to the proximal portion, which acts as a plunger rod during activation of the delivery system. A plurality of slots are provided for controlling the delivery of a substance and extend axially along at least one portion of the holder whereby upon activation of the system, the portions of the holder move towards one another upon the application of a minimum force and the stopper moves a preselected axial distance to expel at least a portion of the substance from the drug container. One application is to a nasal drug container, where approximately equal doses of the substance are desired to be administered to each nostril of the patient.

16 Claims, 11 Drawing Sheets

U.S. PATENT DOCUMENTS

| | | |
|---|---|---|
| 4,599,082 A | 7/1986 | Grimard |
| 4,613,326 A | 9/1986 | Szwarc |
| 4,673,110 A | 6/1987 | Workum |
| 4,767,416 A | 8/1988 | Wolf et al. |
| 4,883,470 A | 11/1989 | Haindl |
| 4,919,167 A | 4/1990 | Manska |
| 4,923,447 A | 5/1990 | Morgan |
| 4,923,448 A | 5/1990 | Ennnis, III |
| 4,929,230 A | 5/1990 | Pfleger |
| 4,944,431 A | 7/1990 | Blake |
| 4,962,868 A | 10/1990 | Borchard |
| 4,964,866 A | 10/1990 | Szwarc |
| 4,966,535 A | 10/1990 | Lina et al. |
| 4,986,818 A | 1/1991 | Imbert et al. |
| 4,994,045 A | 2/1991 | Ranford |
| 5,071,353 A | 12/1991 | van der Wal ............... 434/262 |
| D328,643 S | 8/1992 | Mitchell |
| 5,171,219 A | 12/1992 | Fujioka et al. |
| 5,181,658 A | 1/1993 | Behar |
| 5,284,132 A | 2/1994 | Geier |
| 5,289,818 A | 3/1994 | Citterio et al. |
| 5,331,954 A * | 7/1994 | Rex et al. ............... 128/200.14 |
| 5,368,578 A | 11/1994 | Covington et al. ......... 604/232 |
| 5,427,280 A | 6/1995 | Fuchs |
| 5,431,155 A | 7/1995 | Marelli ....................... 128/200 |
| 5,437,647 A | 8/1995 | Firth et al. .................. 604/110 |
| 5,447,151 A | 9/1995 | Bruna et al. |
| 5,496,286 A | 3/1996 | Stiehl et al. ................ 604/232 |
| 5,511,698 A | 4/1996 | Solignac |
| 5,514,107 A | 5/1996 | Haber et al. ................ 604/197 |
| 5,519,980 A | 5/1996 | Guentert et al. |
| 5,582,598 A | 12/1996 | Chanoch ..................... 604/208 |
| 5,584,417 A | 12/1996 | Graf et al. |
| 5,601,077 A | 2/1997 | Imbert |
| 5,607,400 A | 3/1997 | Thibault et al. |
| 5,630,793 A | 5/1997 | Rowe |
| 5,655,689 A | 8/1997 | Fuchs et al. |
| 5,662,098 A | 9/1997 | Yoshida |
| 5,665,071 A | 9/1997 | Wyrick ....................... 604/134 |
| 5,692,650 A | 12/1997 | Wolter et al. |
| 5,702,362 A | 12/1997 | Herold et al. ................. 604/58 |
| 5,722,956 A * | 3/1998 | Sims et al. .......... 128/DIG. 12 |
| 5,769,325 A | 6/1998 | Jouillat et al. |
| 5,779,677 A | 7/1998 | Frezza ....................... 604/134 |
| 5,813,570 A | 9/1998 | Fuchs et al. |
| D401,323 S | 11/1998 | Ritsche |
| 5,860,567 A | 1/1999 | Fuchs et al. |
| 5,862,962 A | 1/1999 | Fuchs et al. |
| 5,875,938 A | 3/1999 | Graf et al. |
| 5,879,327 A | 3/1999 | DeFarges et al. ............. 604/68 |
| 5,891,085 A | 4/1999 | Lilley et al. ................... 604/68 |
| 5,893,484 A | 4/1999 | Fuchs et al. |
| 5,901,883 A | 5/1999 | Ritsche |
| 5,951,526 A | 9/1999 | Korisch et al. |
| 5,954,695 A * | 9/1999 | Sims et al. .......... 128/DIG. 12 |
| 5,957,897 A | 9/1999 | Jeffrey ........................ 604/223 |
| 5,961,495 A | 10/1999 | Walters et al. .............. 604/208 |
| D418,222 S | 12/1999 | Pellow |
| 6,001,089 A | 12/1999 | Burroughs et al. ......... 604/506 |
| 6,004,299 A | 12/1999 | Arai et al. ................... 604/218 |
| 6,036,675 A | 3/2000 | Thorne et al. .............. 604/232 |
| 6,053,893 A | 4/2000 | Bucher ....................... 604/131 |
| 6,083,197 A | 7/2000 | Umbaugh ..................... 604/68 |
| 6,090,077 A | 7/2000 | Shaw ......................... 604/195 |
| 6,090,080 A | 7/2000 | Jost et al. ................... 604/207 |
| 6,090,082 A | 7/2000 | King et al. .................. 604/234 |
| 6,093,170 A | 7/2000 | Hsu et al. ................... 604/110 |
| 6,112,743 A | 9/2000 | Denton ....................... 128/200 |
| 6,382,204 B1 * | 5/2002 | Jansen et al. .......... 128/200.19 |

FOREIGN PATENT DOCUMENTS

| | | |
|---|---|---|
| EP | 0546607 A1 | 11/1992 |
| EP | 0562943 B1 | 9/1996 |
| EP | 0606672 B1 | 9/1997 |
| EP | 0835820 A1 | 4/1998 |
| EP | 0862921 A2 | 9/1998 |
| EP | 0870699 A3 | 10/1998 |
| EP | 0810955 B1 | 12/1998 |
| EP | 0835820 B1 | 6/1999 |
| FR | 2743353 | 1/1996 |
| FR | 2746657 A1 | 3/1996 |
| FR | 2746676 A1 | 4/1996 |
| FR | 2758801 | 1/1997 |
| FR | 2738555 | 3/1997 |
| FR | 2761281 A1 | 3/1997 |
| FR | 2747451 A1 | 4/1997 |
| FR | 2747926 A1 | 4/1997 |
| FR | 2762589 A1 | 4/1997 |
| FR | 2764807 A1 | 6/1997 |
| FR | 2754453 A1 | 10/1997 |
| FR | 2773135 A1 | 12/1997 |
| FR | 2760195 A1 | 3/1998 |
| FR | 2764375 A1 | 6/1998 |
| FR | 2761667 | 10/1998 |
| JP | 09-8545 | 1/1998 |
| WO | WO 97/01611 | 1/1997 |
| WO | WO 98/06502 | 2/1998 |
| WO | WO 98/34732 | 8/1998 |
| WO | WO 99/32185 | 7/1999 |

* cited by examiner

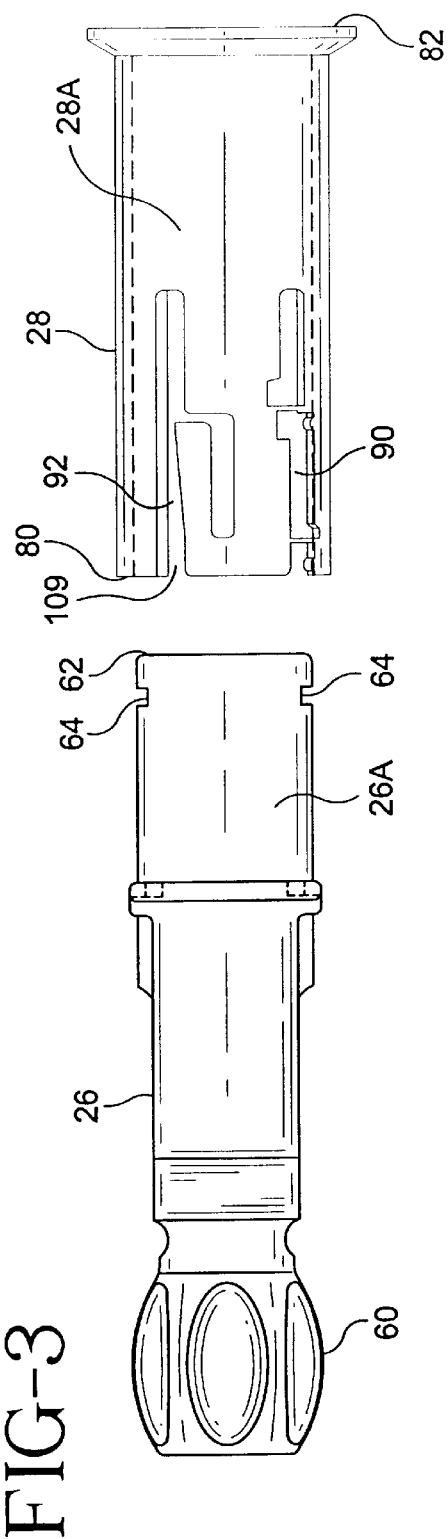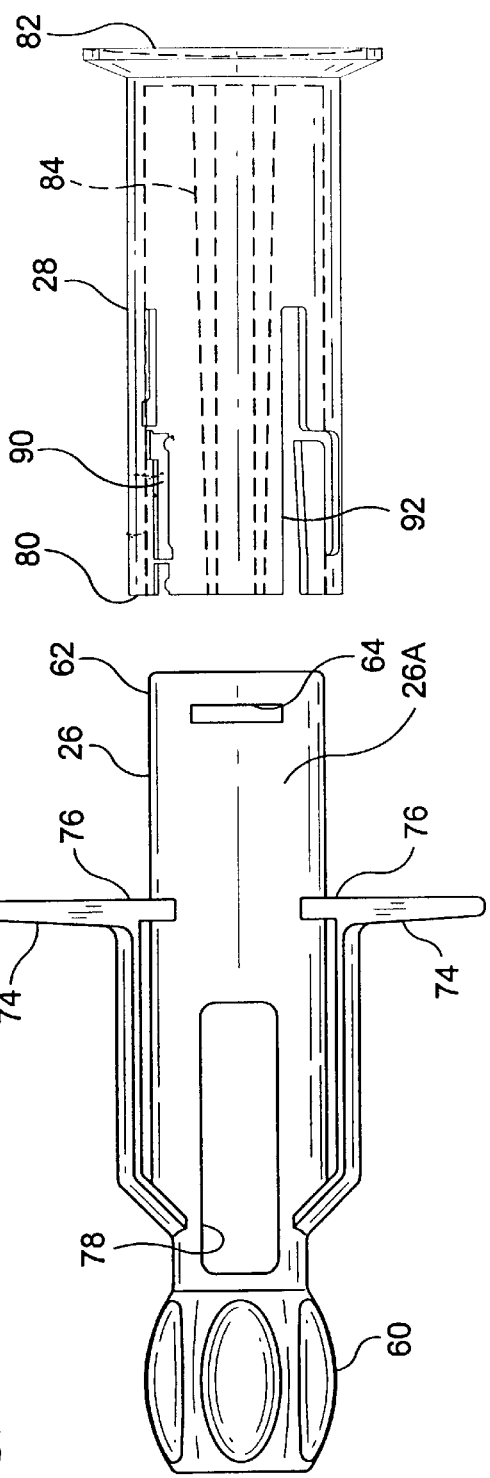

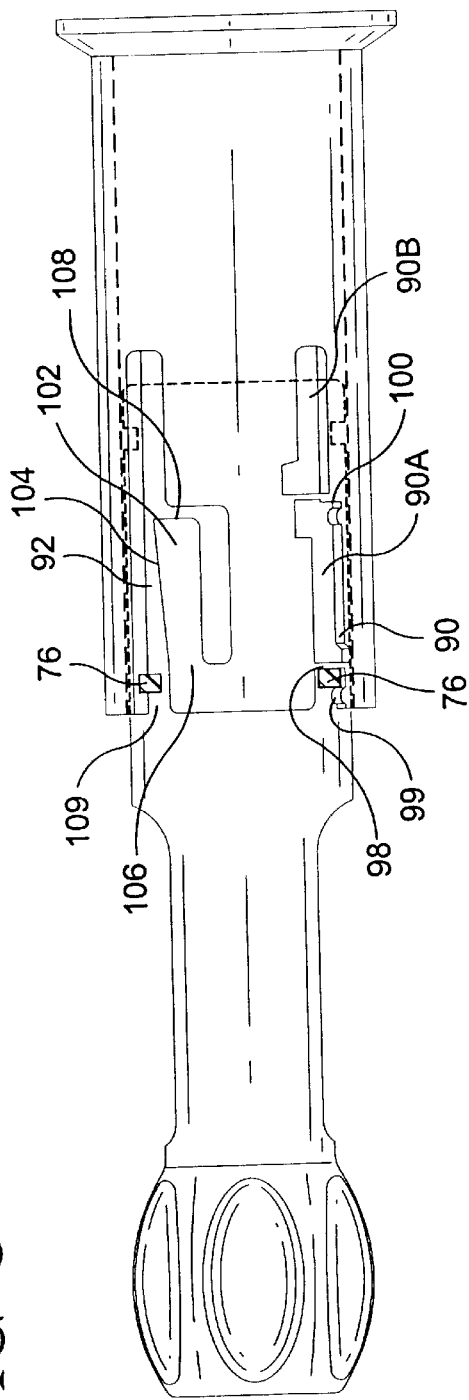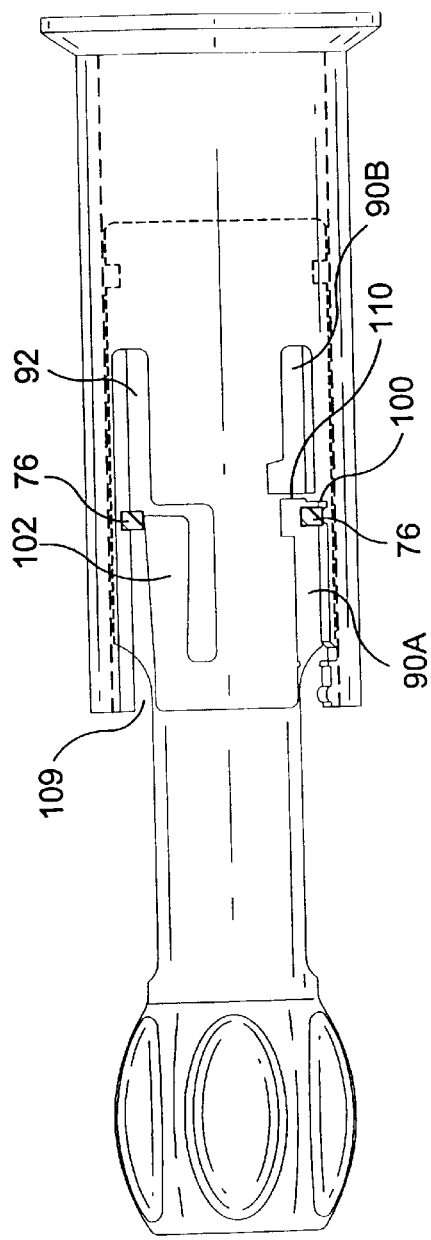
FIG-5
FIG-6

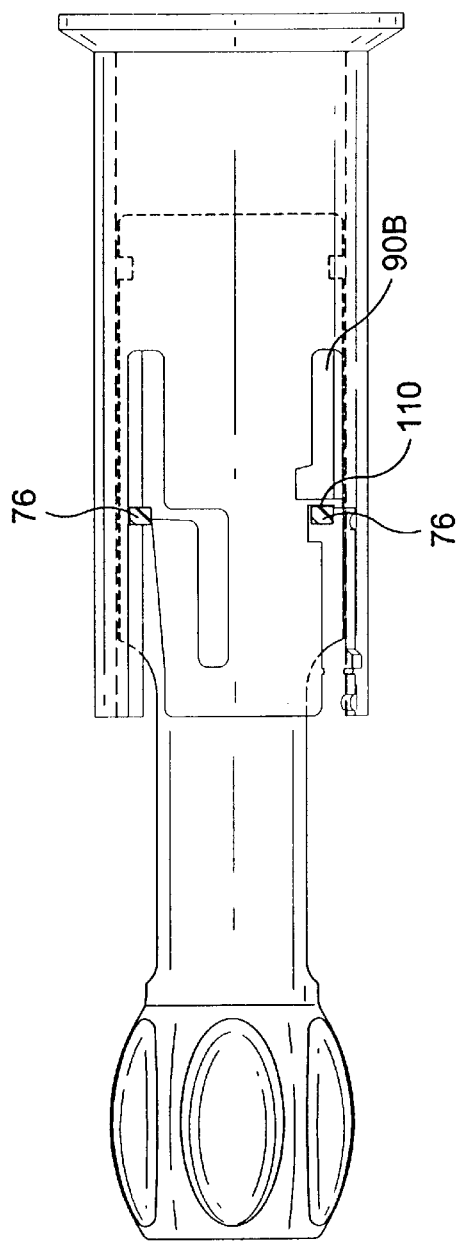
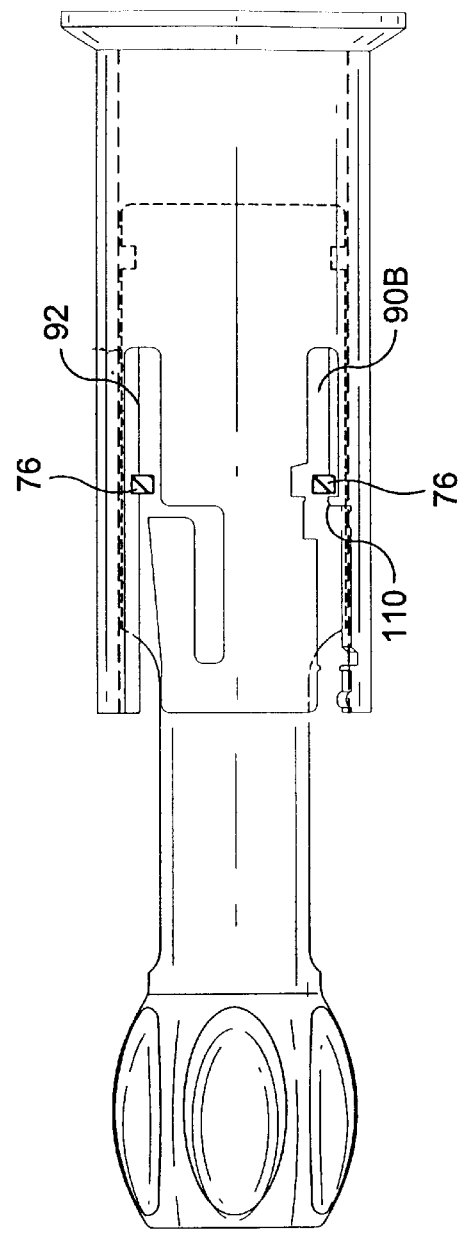
FIG-7
FIG-8

DRUG DELIVERY SYSTEM INCLUDING HOLDER AND DRUG CONTAINER

This is a continuation of application Ser. No. 09/417,346, filed Nov. 14, 1999, now U.S. Pat. No. 6,382,204.

FIELD OF THE INVENTION

The present invention generally relates to delivery systems for delivering substances such as drugs, vaccines and the like, and more specifically relates to a drug delivery device for preferably delivering such substances intranasally, i.e., through the nose, including a holder and a prefilled drug container such as a syringe. In addition, the present invention relates to a holder for use by one hand in which the travel of the stopper is controlled to insure tile application of a minimum force before activation and to divide the substance to be delivered into at least two doses.

BACKGROUND OF THE INVENTION

A number of medications may be effectively administered through the nasal passages. Devices have accordingly been developed for this purpose including either cartridges, such as those described in U.S. Pat. No. 5,893,484 (Fuchs et al.), U.S. Pat. No. 5,813,570 (Fuchs et al.), U.S. Pat. No. 5,655,689 (Fuchs et al.), U.S. Pat. No. 5,511,698 (Solignac), U.S. Pat. No. 5,427,280 (Fuchs), U.S. Pat. No. 5,289,818 (Citterio et al.), U.S. Pat. No. 5,284,132 (Geier) and U.S. Pat. No. 5,171,219 (Fujioka et al.), or syringes, such as those described in U.S. Pat. No. 5,601,077 (Imbert), U.S. Pat. No. 4,923,448 (Ennis, III), U.S. Pat. No. 4,767,416 (Wolf et al.) and U.S. Pat. No. 4,344,573 (De Felice).

The nasal syringes are usually of a more conventional construction such as that described in U.S. Pat. No. 5,601,077 (Imbert) which includes a cylindrical barrel having a blunt tip portion for insertion into a nostril. A stopper is positioned within the barrel. A plunger extends from the end of the barrel opposite to the blunt tip. The plunger controls the position of the stopper within the barrel. A flange may be provided on one end of the plunger to facilitate its use. However, limitations remain, particularly with respect to insuring that sufficient force is applied to the plunger to obtain a therapeutic effective spray.

Nasal syringes are often supplied to users pre-filled with medication. Whether pre-filled or not, it may be desirable to administer selected, and usually equal volumes of medication to each nostril. U.S. Pat. No. 4,962,868 (Borchard) discloses the use of a telescoping tube assembly which is designed for expelling the contents of a nasal syringe in two controlled doses. Also, U.S. Pat. No. 5,601,077 (Imbert) discloses the use of a dose limited in the form of a c-shaped attachment on the plunger rod for limiting movement in the distal directed so that approximately half of the substance to be delivered remains in the syringe. To continue, the user simply removes the attachment from the plunger rod. In addition, U.S. Pat. No. 5,951,526 (Korisch et al.) discloses a holder having an integral dose divider. However, it remains difficult for users to administer equal doses of medication to each nostril, especially with one hand.

Accordingly, there has been a need for a nasal drug delivery device which over comes the problems and limitations associated with the use of the prior devices for delivering a substance, especially intranasally easily with one hand, including delivery of a uniform spray which can be divided into at least two separate doses for delivery into each nostril. Also, there has been a need for a device which would permit the user to observe the substance in the device to determine, for example, if the device has been previously used.

SUMMARY OF THE INVENTION

In contrast to the prior devices discussed above, it has been found that a drug delivery device particularly suited for use in intranasally delivering substances such as drugs, vaccines and the like can be constructed in accordance with the present invention. Specifically, the invention is directed to an assembly such as a housing which allows the use of a conventional, pre-filled drug containers such as syringe while providing control of the dose to be administered. The assembly is particularly applicable to nasal syringes where it is often desirable to dispense medication in two equal doses.

The system of the present invention for delivering at least one substance in at least two doses includes a drug container including a barrel, a first end extending from the barrel, and a stopper slidably positioned within the barrel, a holder having a distal portion and a proximal portion, with the distal portion being assembled to the proximal portion, with the drug container secured therein, and means for controlling the delivery of a substance contained in the barrel of the drug container including a plurality of slots extending axially along at least one of the portions of the holder whereby upon activation of the system, the portions of the holder move towards one another upon the application of a minimum force and the stopper moves a preselected axial distance to expel at least a portion of the substance from the drug container.

In the preferred embodiment of the system, the first end of the drug container includes a spray nozzle for use in intranasally delivering the substance and the drug container is a syringe, and the distal portion of the holder acts as a plunger rod during activation of the system. In addition, the distal portion and the proximal portion of the holder each has a generally tubular interior configured to accommodate the drug container filled with a substance to be delivered and the proximal portion of the holder includes a closed end having a rod extending therefrom for engagement with the stopper of the drug container upon activation. Also, the preselected axial distance corresponds to about a dosage of the substance held in the drug container barrel desired to be administered in a first motion of the stopper, with the preselected axial distance preferably corresponding to about half the distance that the stopper is capable of moving within the barrel to administer about half of the substance held by the drug container.

In addition the preferred system of the present invention includes a means for securing the drug container in the distal portion of the holder with the distal portion having a first end through which the first end of the drug container can extend and a second, open end defining an opening of sufficient size for receiving the drug container. Specifically, the drug container is preferably a syringe having a rim extending from an open end thereof and the drug container securing means is situated adjacent the open end of the distal portion and includes at least one detent situated adjacent the open end and dimensioned so that the rim of the syringe may be securely retained in the distal portion by the detent. Also, a pair of flanges extend radially outwardly from the distal portion of the holder and attached thereto by a plurality of ribs, and the distal portion of the holder includes at least one window to permit visual inspect of the contents of the drug container located within the holder.

Further, the distal portion includes at least one pair of ribs and wherein the slots in the proximal portion of the holder include at least one pair of slots situated thereof, with the pair of slots including a first slot and a second slot extending axially along the body of the proximal portion of the holder generally parallel to each other and dimensioned and situated to accommodate the ribs so that one of the ribs is insertable into each slot and able to travel along the slot upon activation of the system. Also, the first slot is preferably open and is divided into at least two portions, and situated adjacent an open end of the first slot is a bridge extending across at least a portion of the slot, with the bridge being dimensioned so that when a rib comes in contact with the bridge and sufficient force is applied there against, the bridge will fracture to allow passage of the rib alone the slot. In addition, a detent is situated adjacent the open end of the first portion of the first slot so that the rib can be clipped between the detent and the bridge prior to activation of the system, and the second portion of the first slot is at least slightly offset from the first portion of the first slot and towards the second slot, and the other rib travels along the second slot to provide structural stability and tracking, with the second slot including biasing means for biasing the rib in the first slot towards the second portion of the slot upon release of the force applied by a user. The biasing means is adapted to include a cut-away portion forming a deflectable arm having an inner wall associated with the second slot so that as the ribs travel along their respective slots, the one rib will deflect the flexible arm to cause the proximal portion of the holder to rotate relative to the distal portion about a central axis so that the rib situated in the first slot can come in contact with a second bridge so that upon sufficient force being applied, the bridge will fracture to allow passage of the rib along the second portion of the first slot.

The holder of the present invention includes a distal portion and a proximal portion, each configured to accommodate a drug container filled with a substance to be delivered, with the distal portion being able to be assembled to the proximal portion, and means for controlling the delivery of the substance including a plurality of slots extending axially along at least one of the portions of the holder whereby when the portions of the holder are moved towards one another upon the application of a minimum force, at least a portion of the substance can be expelled from the drug container.

In the preferred embodiment of the holder, a first end of the drug container includes a spray nozzle and the drug container is a syringe, and the distal portion and the proximal portion each has a generally tubular interior configured to accommodate the syringe and the proximal portion of the holder includes a closed end having a rod extending therefrom for engagement with the stopper of the syringe during activation.

The system of the present invention for the nasal delivery of at least one substance includes a syringe having a barrel, a first end extending from the barrel, the first end including a spray nozzle having an opening for dispensing the substance from the barrel, and at least one stopper slidably positioned within the barrel, a holder having a distal portion and a proximal portion, each configured to accommodate the syringe, with the distal portion being able to be assembled to the proximal portion, which acts as a plunger rod during activation of the system, and means for controlling the delivery of a substance including a plurality of slots extending axially along at least one of the portions of the holder whereby upon activation of the system, the portions of the holder move towards one another upon the application of a minimum force and the stopper moves a preselected axial distance to expel at least a portion of the substance from the syringe, with the preselected axial distance corresponding to about half the distance that the stopper is capable of moving within the barrel to administer about half of the substance contained by the syringe barrel.

In the preferred embodiment of the system, a pair of flanges extend radially outwardly from the distal portion of the holder and are attached there along by a plurality of ribs, and the distal portion and the proximal portion each have a generally tubular configuration. In addition, the slots in the proximal portion of the holder include two corresponding sets situated on each side thereof with each set including a first slot and a second slot extending axially along the body of the proximal portion of the holder generally parallel to each other and dimensioned and situated to accommodate the ribs so that the ribs are insertable into the slots and able to travel along the slots upon activation of the system, and the first slot is preferably open and is divided into at least two portions, and situated adjacent an open end of the first slot is a bridge extending across at least a portion of the slot, with the bridge being dimensioned so that when a rib comes in contact with the bridge and sufficient force is applied there against, the bridge will fracture or deform to allow passage of the rib along the slot. In addition, a detent is situated adjacent the open end of the first portion of the first slot so that the rib can be clipped between the detent and the bridge prior to activation of the system and the second portion of the first slot is at least slightly offset from the first portion of the first slot and towards the second slot. One of the ribs travels along each of the second slots to provide structural stability and tracking, with each second slot including a cut-away portion forming a deflectable arm for biasing the ribs in the first slots towards the second portions of the slots upon release of the force applied by a user so that as the ribs travel along their respective slots, the ribs traveling along the second slots will deflect the flexible arms to cause the proximal portion of the holder to rotate relative to the distal portion about a central axis so that the ribs situated in the first slots each come in contact with a second bridge so that upon sufficient force being applied, the bridges will each fracture or deform to allow passage of the ribs along the second portions of the first slots.

The method of the present invention for intranasally delivering at least one substance in at least two doses, includes the steps of grasping a pre-assembled drug delivery system with a thumb and two forefingers of one hand, said drug delivery system including a drug container and a holder, with the drug container including a barrel, a first end extending from the barrel, and a stopper slidably positioned within the barrel and the holder having a distal portion and a proximal portion, with the distal portion being assembled to the proximal portion, with the drug container secured therein, and the proximal portion acting as a plunger rod during activation of the system, inserting the end of the drug container into one nostril of a person to whom the substance is to be intranasally delivered, squeezing together the thumb and two forefingers of one hand to apply sufficient force to overcome a bridge extending at least partially across a slot to insure the application of a minimum force, moving the proximal portion of the holder towards the distal portion of the holder a first predetermined distance during a first motion as a result of continuing to squeeze together the thumb and two forefingers to cause the displacement of the stopper and expulsion of a first predetermined amount of a substance contained in the chamber of the drug container barrel into the nostril, removing the end of the drug container from the nostril while relaxing the squeezing force being applied and inserting the end of the drug container into another nostril of the person to whom the substance is to be intranasally delivered, squeezing together the thumb and two forefingers to apply sufficient force to overcome a second bridge extending at least partially across the slot to insure the application of a minimum force, and moving the proximal portion of the holder towards the distal portion of the holder a second predetermined distance during a second motion as a result of continuing to squeeze together the thumb and two forefingers to cause the displacement of the stopper and expulsion of a second predetermined amount of the substance contained in the chamber of the drug container barrel into the other nostril.

In the preferred embodiment of the method, the first predetermined distance is approximately equal to the second predetermined distance and the first predetermined amount of substance expelled is approximately equal to the second predetermined amount of substance expelled. Also, the method includes the step of visually inspecting the contents of the drug container located within the holder through at least one window located in the distal portion of the holder. In addition, relaxing the force being applied during the first motion causes the proximal portion of the holder to rotate about its axis by a force exerted by biasing means. Further, the method includes the step of removing a tip cap from the end of the drug container. The step of grasping the drug delivery device includes placing each of the two forefingers on a flange extending from the distal portion and placing the thumb on a closed end of the proximal portion.

BRIEF DESCRIPTION OF THE DRAWINGS

The various features, objects, benefits, and advantages of the present invention will become more apparent upon reading the following detailed description of the preferred embodiment along with the appended claims in conjunction with the drawings, wherein like reference numerals identify corresponding components, and:

FIG. 3 is a side view of the two portions of the holder prior to assembly;

FIG. 4 is top view of the two portions of the holder prior to assembly;

FIGS. 5–9 are various side views of the holder showing the two portions assembled at various stages of activation to deliver doses of the substance contained therein;

DETAILED DESCRIPTION OF THE INVENTION

Figure 1:
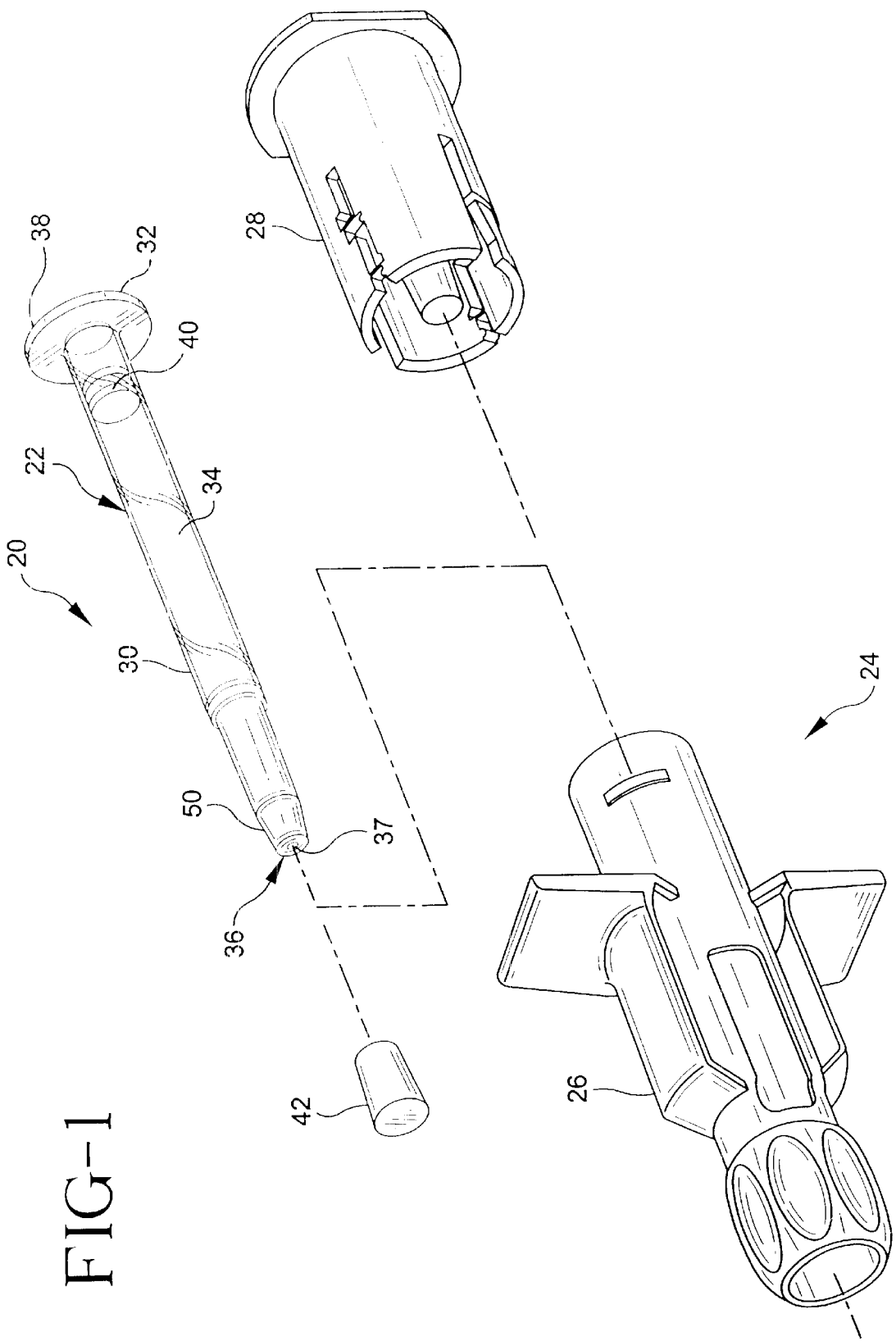
FIG. 1 is an exploded, perspective view of the holder and syringe of the drug delivery system of the present invention.
Figure 2:
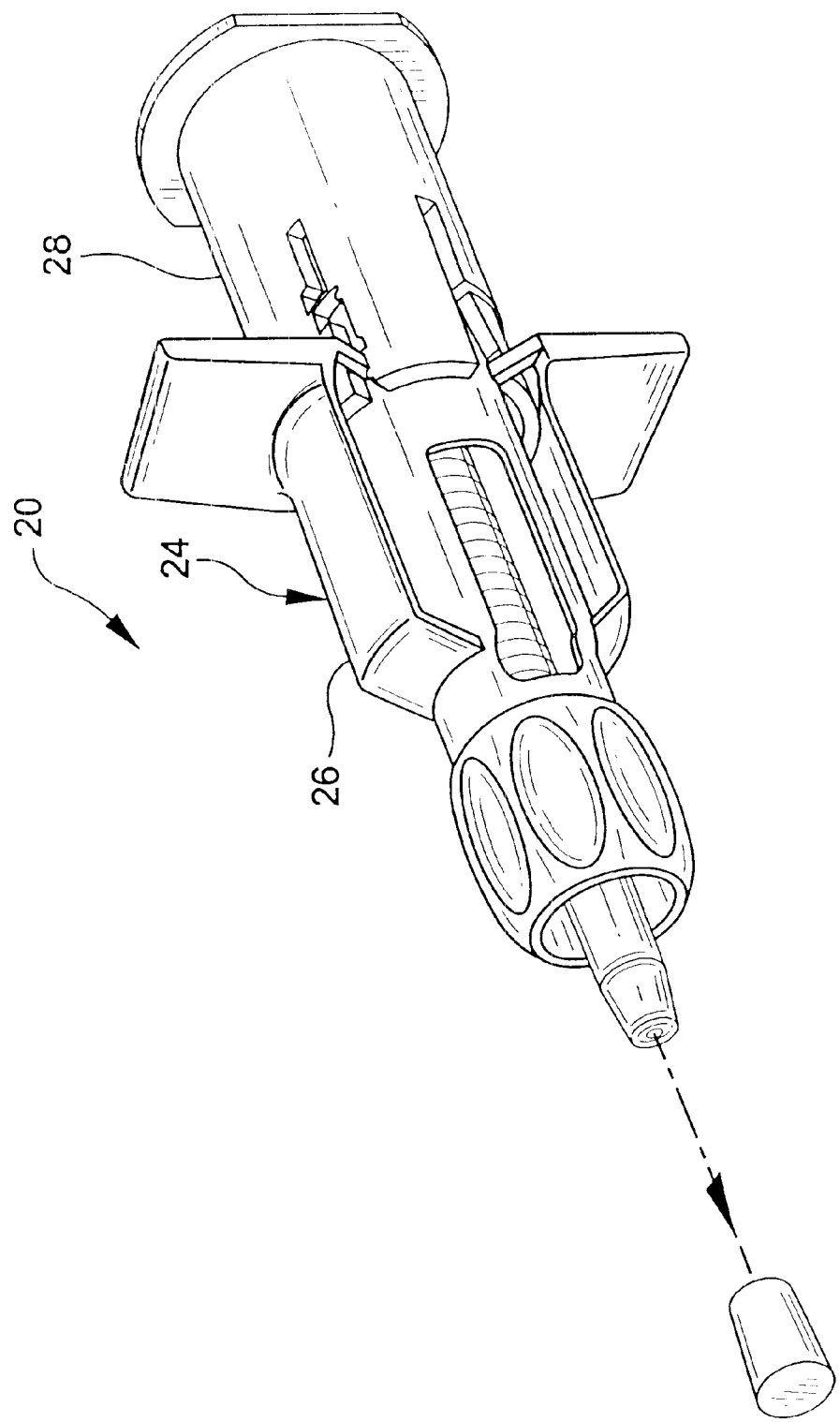
FIG. 2 is a top perspective view of the assembled drug delivery system.

The drug delivery system of the present invention is illustrated in FIGS. 1–15, and generally includes the designation 20. Referring to FIGS. 1 and 2, the system 20 of the present invention includes a drug container such as preferably a syringe 22 and a holder 24. When used to delivery substances intranasally, the assembly insures that the substance to be delivered by the syringe is sprayed into the nostril and can be divided into at least two doses. It further limits the penetration of the syringe tip into the nostril and permits visual inspection of the substance contained in the system.

Referring to FIGS. 1 and 2, the holder 24 for the syringe is comprised of at least two portions, i.e., a distal portion 26 and a proximal portion 28, each have a generally tubular interior configuration to accommodate the syringe 22 therein. For the purposes of the description of the present invention, the term "distal" is meant to refer to the portion or end furthest from the person holding the system of the present invention and the term "proximal" is meant to refer to the portion or end closest to the person holding the system.

The particular syringe of the system is not essential to the present invention and may include, for example, when used to delivery substances intranasally, the nasal syringe disclosed in U.S. Pat. No. 5,601,077 (Imbert), the disclosure of which is hereby incorporated by reference in its entirety. However, preferably, the syringe 22 includes an elongated cylindrical barrel 30 made of either glass or plastic having an open proximal end 32, a chamber 34 for retaining the substance to be delivered and a distal end or tip 36, with the chamber 34 extending from the proximal end to the distal end 36. The distal end includes an orifice 37 through which the substance can be expelled from the chamber. In the preferred embodiment, the proximal end 32 of the syringe includes a rim 38 extending therefrom. The syringe is preferably pre-filled with the substance such as a drug, vaccine or the like to be delivered prior to inserting the syringe into the holder 24.

A stopper 40 is slidably positioned in fluid-tight engagement inside the barrel 30. A sealing or tip cap 42 may be fitted over the tip 36 to prevent the loss of fluid through the orifice prior to use of the assembly.

A spray nozzle 50 extends outwardly from the tip portion of the barrel and includes a conduit therethrough in fluid communication with the orifice. The spray nozzle includes a distal end having a spray aperture in fluid communication with the conduit. It will be apparent to one skilled in the art that there are numerous constructions that can be used to form the spray nozzle and that the arrangement described herein is exemplary of these many possibilities. Also, it is within the purview of this invention to include a valve-less nozzle. Accordingly, the preferred spray nozzle is taught in the prior art and commercially available such as for example from SOFAB of Paris, France and taught in SOFAB's French Patent No. 2,635,084, the disclosure of which is hereby incorporated by reference in its entirety.

Figure 10:
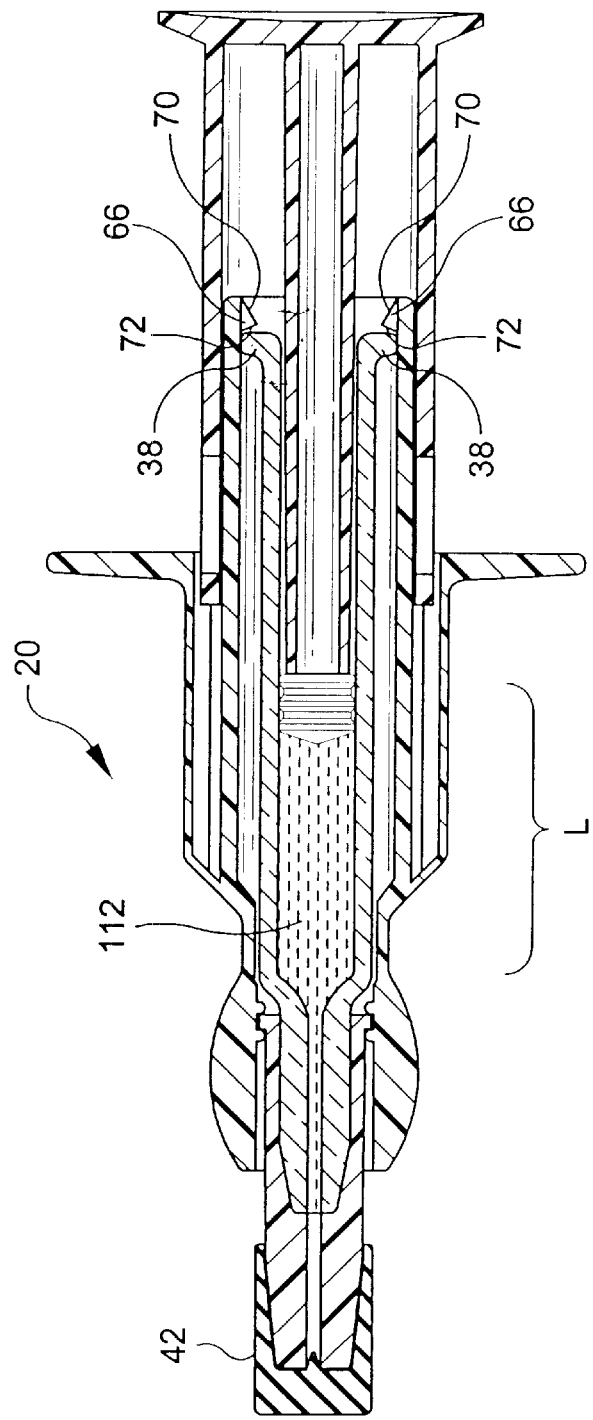
FIGS. 10–12 are various top, sectional views of the syringe and holder at various stages during activation of the drug delivery system showing the position of the plunger within the syringe.
Figure 11:
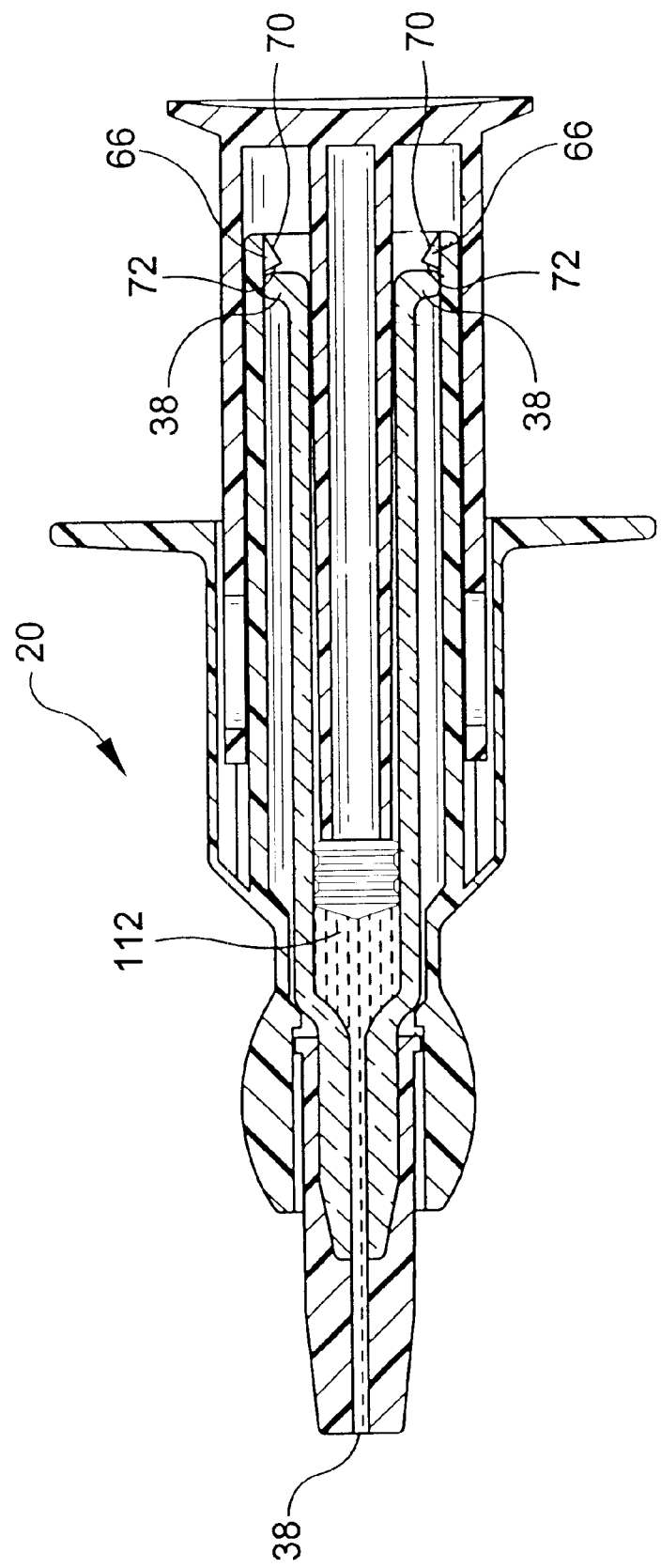
Figure 12:
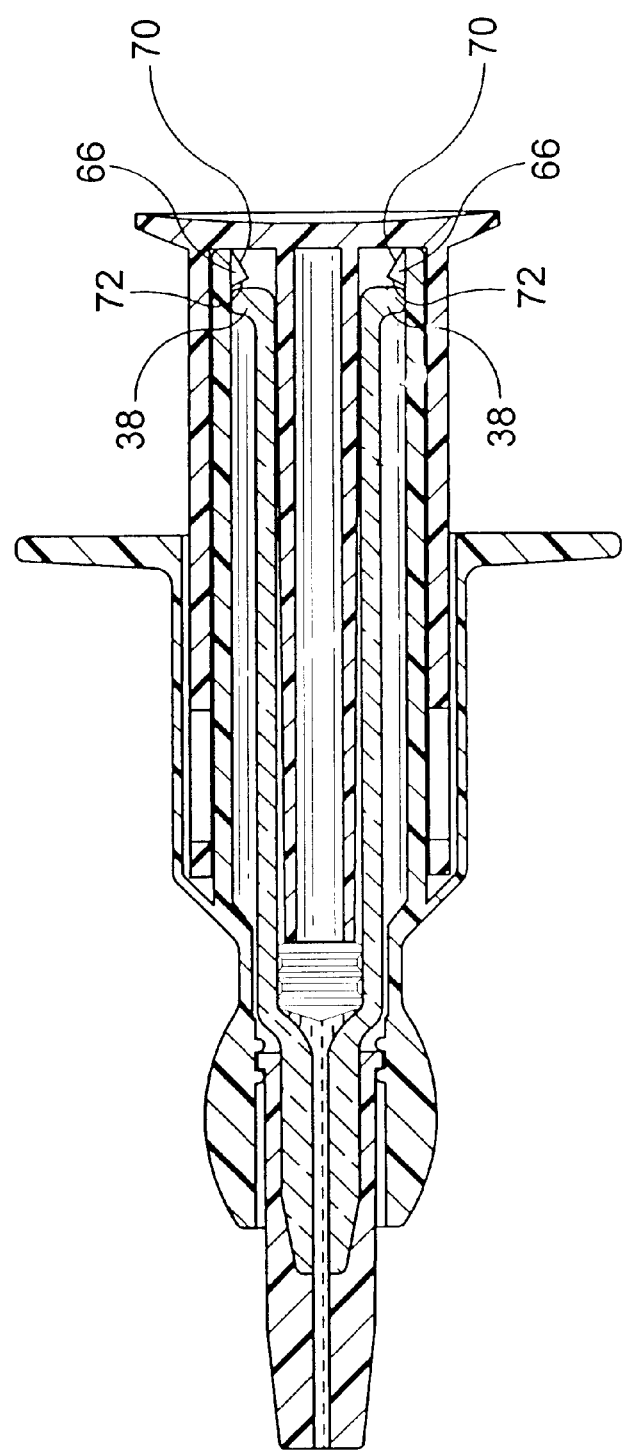

Referring to FIGS. 3 and 4, the two portions 26, 28 of the holder 24 are ergonomically shaped to facilitate handling and preferably have a generally tubular configuration to accommodate the syringe. In addition, the two portions 26, 28 are preferably made from a plastic material such as polypropylene. The distal portion 26 includes an elongated body 26A having a first, enlarged end 60 through which the tip 36, tip cap 42 and spray nozzle 50 can extend, and a second, opened end 62 defining an opening of sufficient size for receiving the syringe barrel, but which is preferably equal in size than the rim 38 through which the syringe may be inserted into the distal portion of the holder. In this way, preferably, the syringe is securely retained in the distal portion of the holder by a pair of grooves 64 and detents 66 as shown in FIGS. 10–12, situated proximally to the open end and dimensioned so that the rim of the syringe may extend therefrom. To facilitate insertion of the rim past the detents, as well as inhibit removal of the syringe from the holder, a projection to form the detent 66, as well as the groove, is situated adjacent each groove for retaining the syringe in the distal portion 26 of the holder 24 (FIGS. 10–12). Each detent 66 includes angled end face 70 and a shoulder portion 72 defined by the inner surface of the detent which allows the rim of the syringe to snap behind the detents and lock the rim of the syringe in place.

In addition, a pair of flanges 74 extending radially outwardly from the first end 60 towards the second open end 62 and are attached therealong by a plurality of ribs 76 (FIG. 4). The front end 60 is larger in diameter than the diameter of an average adult nostril, and is blunt. While the embodiment shown in the drawings has a front end face which is rounded, it may alternatively be oval or any other shape desired, provided that the front end face is prevented from entry into the nostril.

One or more windows 78 are provided in the body 26A of the distal portion of the holder (FIG. 4). The windows may be in the form of openings in the body, or transparent wall portions mounted to the body. The windows allow the user to view the syringe barrel located within the holder. The user can accordingly determine whether there is any substance present in the syringe, and whether the substance is suitable for administration. As some pharmaceutical products are frozen during storage, it may be important to determine whether the product within the syringe has thawed prior to administration.

The proximal portion 28 of the holder is designed to be assembled to the distal portion 26 and preferably acts as a plunger rod during activation of the system. In addition, the proximal portion includes a means for controlling delivery of the substance, as well as to divide the substance into at least two doses. Specifically, the proximal portion includes an end face defining an opening 80 of sufficient size for accommodating at least a portion of the body 26A of the distal portion 26 of the holder. In the preferred embodiment, the other end 82 is closed and includes an elongated rod 84 integrally formed in the proximal portion of the holder and extending from the closed end 82 towards the open end 80. The rod 84 is of a sufficient size and dimension to engage the stopper during activation of the system. However, it should be appreciated that a conventional plunger rod may be utilized with the syringe instead of having an integrally formed rod 84 in the holder.

Referring to FIGS. 3–9, the means utilized to control delivery of the substance includes a plurality of slots extending axially along the body of the proximal portion of the holder. The slots are preferably provided in two corresponding sets situated on each side thereof. Specifically, each set includes a first slot 90 and a second slot 92 extending axially along the body of the proximal portion of the holder generally parallel to each other. The slots are dimensioned and situated about the body 28A of the proximal portion 28 of the holder to accommodate the ribs 76 connecting the flanges 74 to the body 26A of the distal portion 26 so that the ribs are insertable into the slots and able to travel along the slots upon activation of the system.

Referring to FIG. 5, the first slot 90 is preferably open and is divided into at least two portions 90A, 90B when the system is to be used to deliver at least two doses of the substance, with each portion 90A, 90B having a length corresponding to the desired distance in which the stopper must travel to expel the substance from the chamber of the syringe barrel. Situated adjacent the open end of the slot 90 is a bridge 98 extending across at least a portion of the slot, and preferably bridging the entire gap of the slot. The bridge is dimensioned so that when a rib 76 comes in contact with the bridge and sufficient force is applied there against, the bridge will fracture and allow passage of the rib along the slot. In this way, the rib will travel along the slot until is comes in contact with a stop 100 situated at the end of the first portion 90A of the slot 90. The second portion 90B of the slot 90 is preferably slightly offset from the first portion 90A of the slot and towards the other slot 92.

A detent 99 is situated adjacent the open end 80 of the proximal portion of the holder along the slot 90 so that the rib can be clipped or snapped between the detent 99 and the bridge 98 prior to activation of the system.

Figure 9:
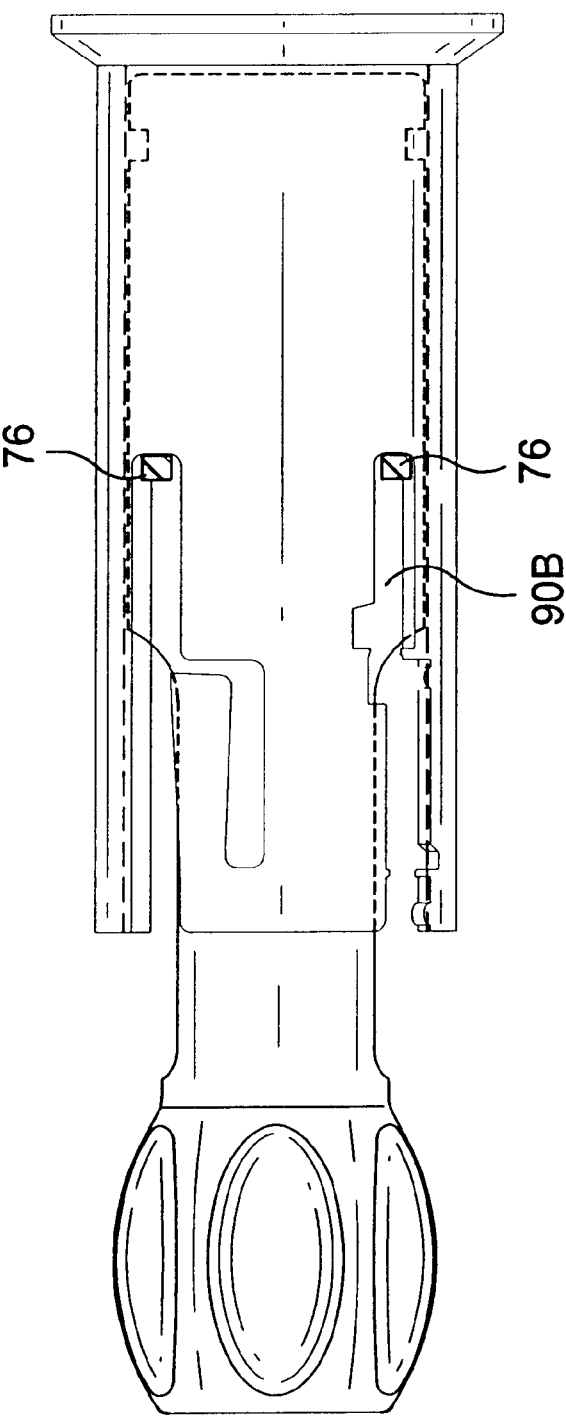

In addition, a corresponding rib 76 travels along the other or second slot 92 to provide structural stability and tracking, and the other slot 92 includes a biasing means to bias the rib in the first slot towards the second portion of the slot upon releasing/relaxing of the force applied by the user. Specifically, the other slot 92 includes a cut-away portion forming a deflectable arm 102 having a inner wall 104 associated with the slot slightly inclined and an upper portion 106 having a width less than a lower extending portion 108 and the slot 92 being wider at an open end 109 and narrowing along the slightly inclined inner wall 104 of the deflectable arm 102 (FIGS. 5 and 6). In this way, as the two ribs 72 travel along their respective slots 90, 92, the one rib traveling along slot 92 will deflect the flexible arm 102 to cause the proximal portion 28 of the holder to rotate relative to the distal portion 26 about its central axis, and the rib 76 traveling along slot 90 will move along the stop 100 and adjacent a bridge 110 similar to the first bridge but extending across the second portion 90B of the slot before traveling along the second portion 90B of the slot 90 (FIG. 7). Accordingly, upon sufficient force being applied, the bridge 110 will fracture to allow passage of the rib 76 into the second portion 90B of the slot (FIG. 8) and there along until it reaches the bottom of the slot (FIG. 9). It should also be appreciated that the inclined inner wall may have sufficient flexibility to provide the necessary biasing to cause relative rotation.

It should be appreciated that for purposes of illustration, the device has been described with respect to one set of slots and ribs. However, a corresponding arrangement is preferably provided on the other side of the holder. Also, it should be apparent that the slot can be divided into successive portions to further divide the substance to be delivered into additional doses.

Although the system of the present invention has been described in connection with preferably the use of a nasal syringe, it should be appreciated that the holder may also be used in connection with syringes having needles such as those described in U.S. Pat. No. 4,964,866 (Szwarc), U.S. Pat. No. 4,986,818 (Imbert et al.) and U.S. Pat. No. 5,607,400 (Thibault et al.), the disclosures of which are hereby incorporated by reference in their entirety as though fully set forth herein.

Also, it should be appreciated that although the preferred embodiment has been described in connection with a single compartment syringe, a multi-compartment syringe (not shown) can be utilized where, for example, a diluent is provided in one chamber and at least one dry or wet substance is provided in another chamber such as those described in U.S. Pat. No. U.S. Pat. No. 4,599,082 (Grimard), U.S. Pat. No. 4,613,326 (Szwarc), U.S. Pat. No. 4,929,230 (Pfleger) and U.S. Pat. No. 4,235,235 (Bekkering), the disclosures of which are hereby incorporated by reference as though fully set forth herein. In this way, the first portion of the slot can be used to permit the stopper to travel a sufficient distance so as to permit mixing of the two substances. Thereafter, travel of the stopper permits the reconstituted substance to be delivered. Also, under such circumstances the initial bridge may be eliminated or reduced to a detent for merely attaching the two portions of the holder together.

The syringe 22 is preferably filled with the substance to be delivered and stoppered prior to assembly with the holder 24. In this way, the prefilled syringe can be inserted into the distal portion 26 of the holder and secured therein as a result of the rim of the syringe coming in contact with the detent 66 and in front of the grooves 64. Then the proximal portion 28 of the holder can be secured to the distal portion 26 of the holder by inserting the ribs 76 of the flanges 74 into the initial portion of each slot between the detents 99 and the bridges 98.

Operation and Use

Having described the preferred embodiment of the drug delivery system 20 of the present, including the assembly thereof, its operation and use is described below in connection with FIGS. 5–12, and in particular FIGS. 13 and 14, with FIGS. 5 and 10 illustrating the system prior to activation.

Figure 13:
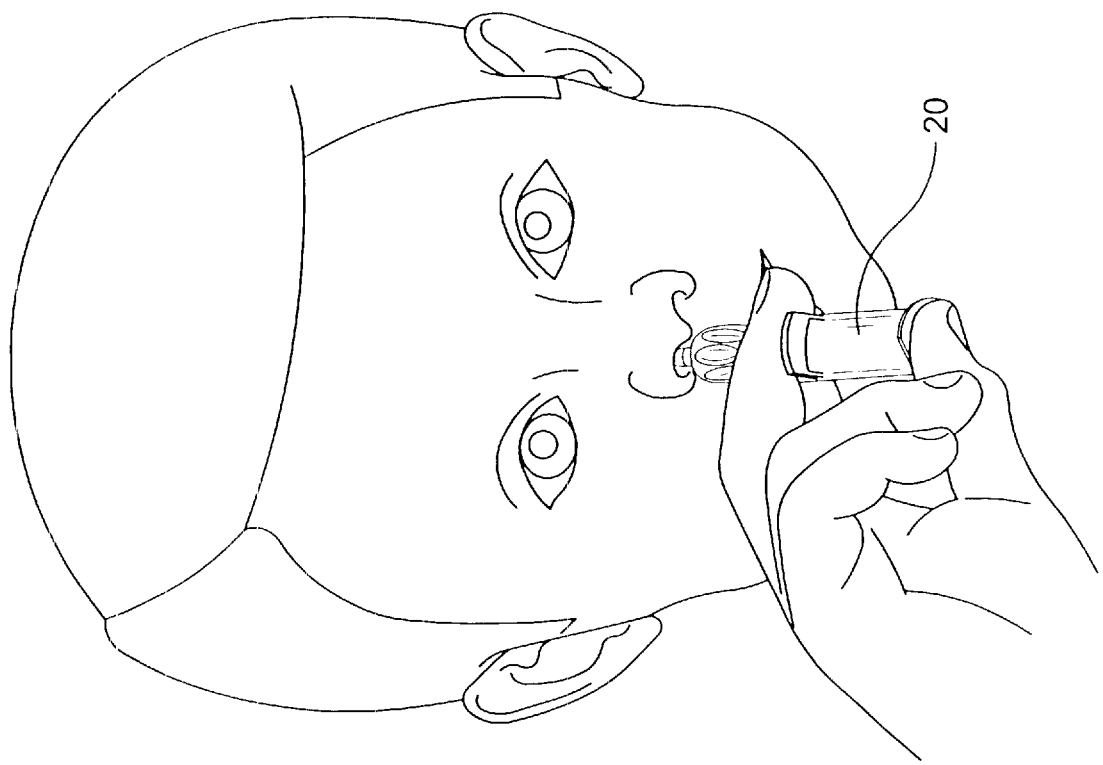
FIGS. 13 and 14 are schematic representations of the drug delivery device of the present invention being used to deliver the substance to each of the nostrils of the user.
Figure 14:
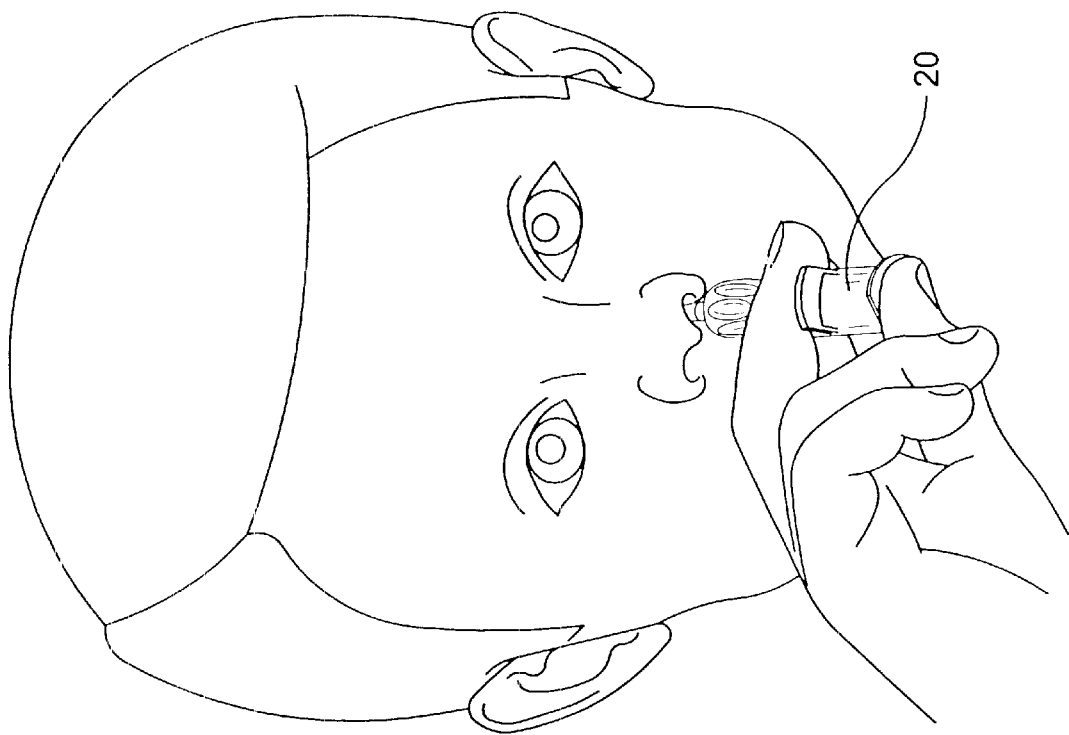

In operation, the user grasps the pre-assembled system 20 as shown in FIG. 13 and with the tip cap 42 removed, insert the blunt tip into one nostril. The proximal portion of the holder is then moved towards the distal portion of the holder by the user squeezing together his thumb and two forefingers so that the two portions move towards each other with the proximal portion acting as a plunger rod (FIGS. 5 and 6). This movement, causes the displacement of the stopper 40 and expulsion of a predetermined amount of the substance 112 contained in the chamber of the syringe barrel through the orifice 37, depending upon the distance that the proximal portion, as well as the rod, travels until its progress is arrested by first stop, as shown in FIG. 11. For simplicity, the total distance that the stopper 40 may be displaced into the barrel 30 of the syringe 22 is depicted by the legend "L" in FIG. 10, with that distance "L" also correlating to the total quantity of substance retained in the syringe barrel. Similarly, the displacement of the stopper a distance L/n, would correlate to a first desired quantity of the substance to be administered from the syringe during a first motion of the proximal portion. For instance, for an application to a nasal syringe, it is typically desirable to ensure equal administration of the substance into each of the nostrils, meaning that it would be desirable to expel only half of the contents of the syringe at such time as the rib is arrested by the first stop (thus, L/n would correlate to L/2).

After a first administration of the substance, then the user would remove the system 20 from that nostril and place it in the other nostril (FIG. 14), naturally relaxing the pressure or force being applied to the system resulting in the proximal portion of the holder rotating about its axis by the force exerted by the flexible arm so as to put the rib in position to travel along the second portion of the slot adjacent the second bridge (FIG. 7). Once the rib is so situated and the system situated in the other nostril, the proximal portion of the holder is again squeezed, causing the rod to advance and fracture bridge 110 (FIG. 8) and engage the stopper to expel the remaining contents of the syringe into the other nostril. FIGS. 9 and 12 show the system 20 once the contents have been expelled. Once so used, the entire system is typically discarded.

The system 20 provides a number of advantageous features. It allows the user to easily divide the dose to be delivered from the syringe using only one hand to position and activate the system. When used with a nasal syringe, the enlarged end of the holder limits the penetration of the syringe tip into the nostril. In addition the overall configuration of the holder together with its enlarged flanges facilitates its handling and use with only one hand.

Figure 15:
FIG. 15 is a fragmentary, sectional view of an alternative embodiment of the drug delivery system illustrating securement of the syringe in the holder.

As illustrated in FIG. 15, in the alternative, the syringe may be retained in the distal portion of the holder by a pair of detents or a groove 200 running along the tip in which a corresponding rim on the spray nozzle can be inserted.

While the preferred embodiment of the present invention has been described so as to enable one skilled in the art to practice the device of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. A method of intranasally delivering at least one substance in at least two doses, comprising the steps of:

grasping a pre-assembled drug delivery system with a thumb and two forefingers of one hand, said drug delivery system including a drug container and a holder, with the drug container including a barrel, a first end extending from the barrel, and a stopper slidably positioned within the barrel and the holder having a distal portion and a proximal portion, with the distal portion being assembled to the proximal portion, with the drug container secured therein, and the proximal portion acting as a plunger rod during activation of the system;

inserting an end of said drug container into a first nostril of a person to whom the substance is to be intranasally delivered;

squeezing together the thumb and two forefingers of the one hand to apply sufficient force to break a first frangible bridge extending across a slot to insure the application of a minimum force;

moving the proximal portion of the holder towards the distal portion of the holder a first predetermined distance during a first motion as a result of continuing to squeeze together the thumb and two forefingers to cause a first displacement of the stopper and expulsion of a first predetermined amount of a substance contained in the chamber of the drug container barrel into said first nostril;

removing the end of said drug container from said first nostril while relaxing the squeezing force being applied and inserting the end of said drug container into a second nostril of the person to whom the substance is to be intranasally delivered;

squeezing together the thumb and two forefingers to apply sufficient force to break a second frangible bridge extending across the slot to insure application of a minimum force; and moving the proximal portion of the holder towards the distal portion of the holder a second predetermined distance during a second motion as a result of continuing to squeeze together the thumb and two forefingers to cause a second displacement of the stopper and expulsion of a second predetermined amount of the substance contained in the chamber of the drug container barrel into said second nostril.

2. The method described in claim 1 wherein said first predetermined distance is approximately equal to said second predetermined distance and said first predetermined amount of substance expelled is approximately equal to said second predetermined amount of substance expelled.

3. The method described in claim 1, further comprising the step of visually inspecting the substance in the drug container located within the holder through at least one window located in said distal portion of said holder.

4. The method described in claim 1, wherein relaxing the force being applied during said first motion causes the proximal portion of the holder to rotate about a longitudinal axis by a force exerted by biasing means.

5. The method described in claim 1, wherein the step of grasping the drug delivery includes placing each of the two forefingers on a flange extending from the distal portion of the holder and placing the thumb on a closed end of the proximal portion of the holder.

6. The method described in claim 1, further comprising the step of removing a tip cap from said first end of said barrel of said drug container before inserting the end of said drug container into said first nostril of the person to whom the substance is to be intranasally delivered.

7. A system for delivering at least one substance in at least two doses, comprising:
a drug container including an open end and a stopper slideably positioned with said container;
a holder surrounding said drug container including a first generally tubular body portion having an open end and a second generally tubular body portion having an open end telescopically received in said open end of said first generally tubular body portion;
one of said generally tubular body portions including at least two circumferentially spaced ribs and the other of said generally tubular body portions including two generally axially extending circumferentially spaced slots receiving said circumferentially spaced ribs including a first slot including a first axially extending slot portion adjacent said open end and a second axially extending slot portion circumferentially offset from said first axially extending slot portion; and
a second slot of said generally axially extending circumferentially spaced slots including a deflectable side wall extending into said second slot generally circumferentially aligned with an intersection of said first and second axially extending slot portions of said first slot, said deflectable side wall rotating said other of said generally tubular body portions to align said rib in said first axially extending slot portion with said second axially extending slot portion when said rib in said second slot is generally circumferentially aligned with said intersection of said first and second axially extending slot portions.

8. The system as defined in claim 7, wherein said deflectable side wall of said second slot is formed by a deflectable arm having a first end portion integral with said other of said generally tubular body portions and a second free end portion extending into said second slot.

9. The system as defined in claim 7, wherein said intersection of said first and second axially extending slot portions of said first slot includes an integral frangible bridge portion at said intersection.

10. The system as defined in claim 7, wherein said first slot includes an opening through said open end of said other of said generally tubular body portions and an integral frangible bridge portion located between said opening through said open end of said other of said generally tubular body portions and said first axially extending slot portion.

11. A system for delivering at least one substance in at least two doses, comprising:
a drug container including an open end and a stopper slideably positioned within said container;
a holder surrounding said drug container including a first generally tubular body portion having an open end and a second generally tubular body portion having an open end telescopically received in said open end of said first generally tubular body portions;
one of said generally tubular body portions including at least two circumferentially spaced ribs and the other of said generally tubular body portions including two generally axially extending circumferentially spaced slots receiving said circumferentially spaced ribs including a first slot having an opening through said open end of said other of said generally tubular body portions, a first axially extending slot portion adjacent said opening and a second axially extending slot portion circumferentially offset from said first axially extending slot portion; and
an integral frangible bridge portion extending between said opening through said open end of said other of said generally tubular body portions and said first axially extending slot portion.

12. The system as defined in claim 11, wherein a second slot of said generally axially extending circumferentially spaced slots includes a deflectable side wall extending into said second slot generally circumferentially aligned with an intersection between said first and second axially extending slot portions of said first slot, said deflectable side wall rotating said other of said generally tubular body portions to align said rib with said second axially extending slot portion when said rib is located in said second slot, said deflectable side wall generally circumferentially aligned with said intersection of said first and second axially extending slot portions.

13. The system as defined in claim 11, wherein said intersection of said first an second axially extending slot portions of said first slot includes an integral frangible bridge portion.

14. A method of intranasally delivering at least one substance in at least two doses, comprising the following steps:
grasping a pre-assembled drug delivery system with a thumb and forefingers, said drug delivery system including a drug container and a holder, with said drug container including an open end, a stopper slideably received in the container and a drug in the drug container between the stopper and the open end, and said holder surrounding said drug container including a first body portion telescopically received in a second body portion and telescopic movement of the second body portion into the first body portion drives said stopper toward said open end upon actuation of the system, said first body portion including a radial rib and said second body portion including a generally axially extending slot receiving said rib including a first slot portion and a second slot portion circumferentially offset from said first slot portion;
inserting said open end of said drug container in a first nostril of a person to whom said drug is to be intranasally delivered;
applying a squeezing force by squeezing together said first and second body portions of said holder to drive said rib through said first slot portion, driving said stopper toward said open end of said container a predetermined distance equal to the length of said first slot portion to deliver a first dose of said drug into said first nostril;

removing said open end of said drug container from said first nostril while relaxing said squeezing force applied to said first and second body portions;

said first and second body portions then relatively rotating without manual manipulation to receive said radial rib opposite said second slot portion;

inserting said open end of said drug container in a second nostril of the person to whom said drug is to be intranasally delivered; and squeezing together said first and second body portions of said holder to drive said stopper toward said open end of said container a distance equal to said second slot portion to deliver a second dose of said drug to said second nostril.

15. The method as defined in claim 14, wherein said slot includes an opening receiving said rib and a first integral frangible bridge located between said opening and said first slot portion, wherein said method includes squeezing together said first and second body portions with sufficient force to break said first integral frangible bridge to receive said rib in said first slot portion.

16. The method as defined in claim 14, wherein said generally axially extending slot includes a second integral frangible bridge located between said first and second slot portions, wherein said method includes squeezing together said first and second body portions with sufficient force to break said second integral frangible bridge to receive said rib in said second slot portion.

* * * * *